US006574808B1

(12) United States Patent
Brown et al.

(10) Patent No.: US 6,574,808 B1
(45) Date of Patent: Jun. 10, 2003

(54) IMAGING TABLE LEVELING SYSTEM

(75) Inventors: Stephen James Brown, West Valley City, UT (US); Jeffrey Wayne Pattee, Salt Lake City, UT (US); Robert William Odell, North Salt Lake City, UT (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 166 days.

(21) Appl. No.: 09/690,496

(22) Filed: Oct. 17, 2000

(51) Int. Cl.[7] ............................................... A61G 13/04
(52) U.S. Cl. .............................................. 5/601; 5/608
(58) Field of Search ....................... 5/600, 601, 607, 5/608, 610; 378/209; 108/6, 7, 8

(56) References Cited

U.S. PATENT DOCUMENTS

| 4,229,656 A | * | 10/1980 | Iversen et al. ............... 378/178 |
| 4,761,000 A | | 8/1988 | Fisher et al. ................. 269/323 |
| 4,769,584 A | * | 9/1988 | Irigoyen et al. .............. 318/654 |
| 5,161,274 A | * | 11/1992 | Hayes et al. ..................... 5/618 |
| 5,205,004 A | * | 4/1993 | Hayes et al. ..................... 5/611 |
| 5,611,096 A | * | 3/1997 | Bartlett et al. .................. 5/617 |
| 6,275,568 B1 | * | 8/2001 | Prins et al. .................. 378/158 |
| 6,353,949 B1 | * | 3/2002 | Falbo ............................. 5/610 |
| 6,353,950 B1 | * | 3/2002 | Bartlett et al. .................. 5/617 |
| 6,375,352 B1 | * | 4/2002 | Hewes et al. ............... 378/196 |
| 6,421,854 B1 | * | 7/2002 | Heimbrock .................... 5/610 |
| 2002/0104164 A1 | * | 8/2002 | Heimbrock .................... 5/610 |
| 2003/0000016 A1 | * | 1/2003 | Zenczykowski ............... 5/600 |

FOREIGN PATENT DOCUMENTS

DE 44 16 689 C1 6/1995
EP 0488 552 A3 6/1992

* cited by examiner

Primary Examiner—Robert G. Santos
(74) Attorney, Agent, or Firm—McAndrews, Held & Malloy, Ltd.; Peter J. Vogel; Michael A. Dellapenna

(57) ABSTRACT

An imaging table leveling system for use with a medical imaging device is provided which levels an imaging table with respect to true level. The imaging table leveling system levels an imaging table before the imaging table is floated, or while the imaging table is floating. The system includes an imaging table, an inclinometer, a processor, and actuators. The inclinometer continuously measures table angle data. When activated, the processor receives the table angle data from the inclinometer. The processor then compares the table angle data to a stored level constant. The stored level constant is a measurement of true level. The processor then commands the actuators to move the imaging table until the table angle data matches the stored level constant. The table angle data is also used to correct differences in actuator rates during tilt or roll motions.

16 Claims, 2 Drawing Sheets

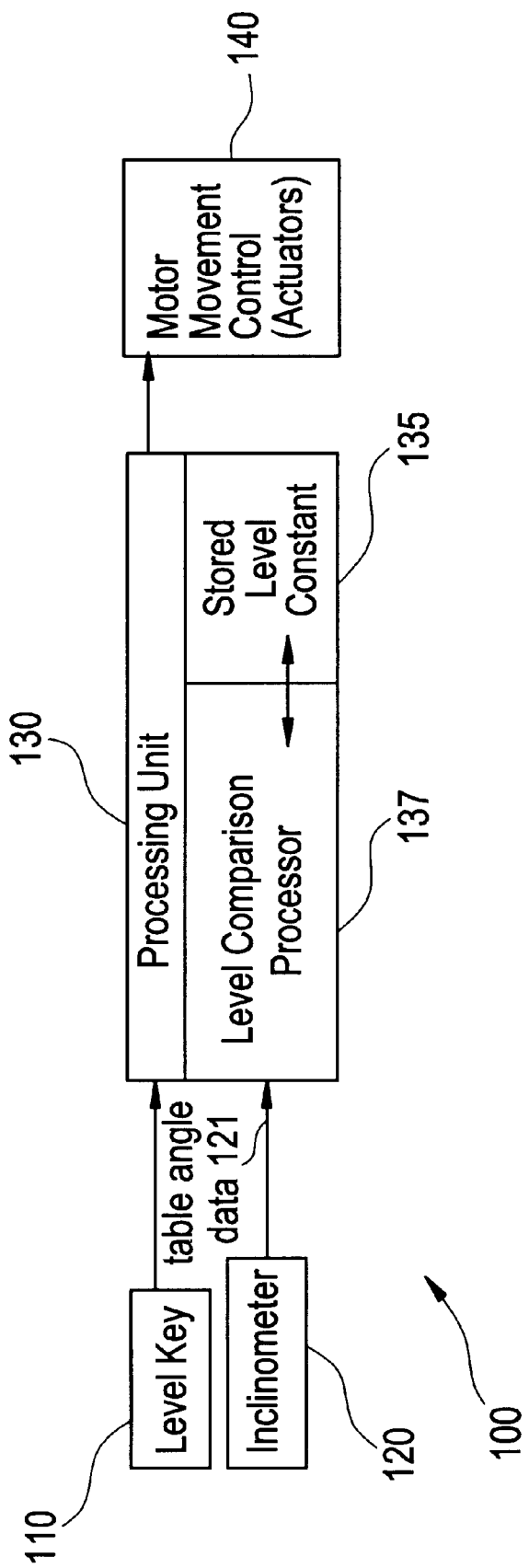

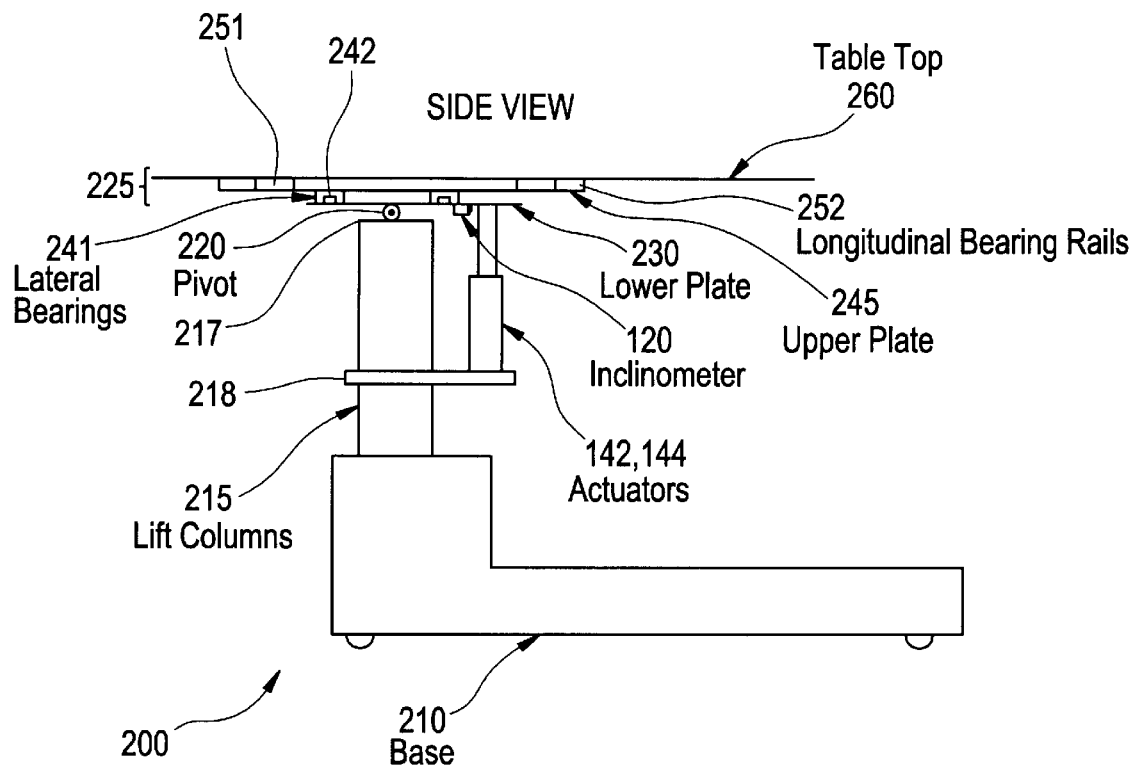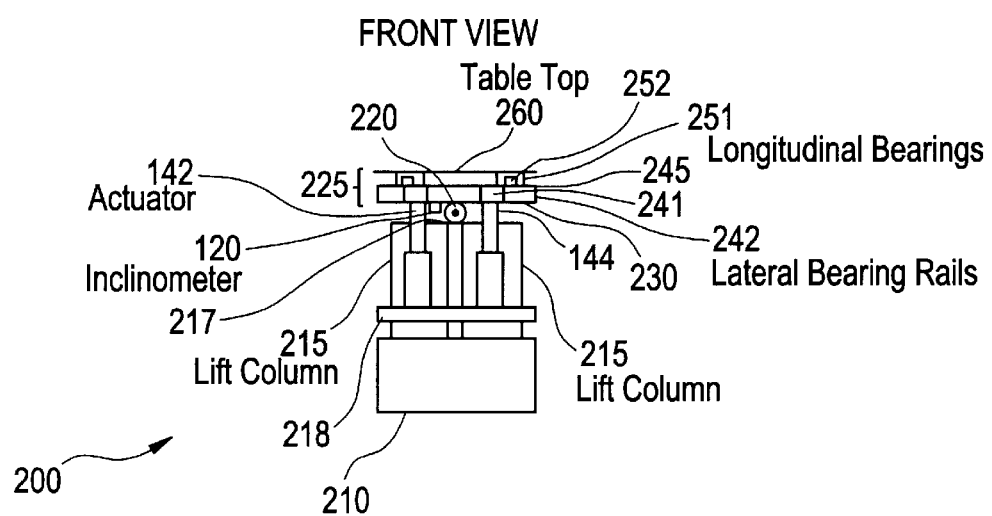

IMAGING TABLE LEVELING SYSTEM

FIELD OF THE INVENTION

The present invention relates to an imaging table leveling system for use with a medical imaging device. More particularly the invention relates to an imaging table leveling system that levels an imaging table with respect to true level and automatically corrects table level during tilt and roll.

BACKGROUND OF THE INVENTION

Medical imaging systems typically include an emitter, a detector, and an imaging table. In operation, the imaging table, on which patients are positioned, is positioned between the emitter and the detector. The emitter typically emits radiation, such as X-rays, toward the detector. The radiation typically passes through the patient positioned on the imaging table and encounters the detector. As the radiation passes through the patient, anatomical structures inside the patient cause spatial variances in the radiation received at the detector. The detector then translates the radiation variances into an image which may be employed for clinical evaluations.

As mentioned above, while imaging, the patient is positioned on an imaging table. The imaging table supports the patient but is mostly transparent to the imaging radiation so as to not interfere with the imaging of the patient. Proper positioning of the patient on the imaging table is important for a variety of reasons. For example, some imaging devices operate in confined areas. Further, positioning a patient within the imaging chamber of an imaging device may be awkward and difficult. In addition, medical procedures may be intricate and complex. Stopping a procedure to reposition a patient for imaging may be a time consuming and dangerous event. Medical imaging systems, such as X-ray imaging systems, often require extensive imaging of various portions of a patient's body.

In order to assist in the proper positioning of the patient, some imaging tables may be re-positioned during imaging. The process of re-positioning the imaging table, or floating, typically makes the imaging process quicker and easier.

Typically, the imaging table must be level before it is floated for two reasons: First, medical images are typically more accurate when the imaging table is level. Images of the patient may be distorted if the imaging device images a patient positioned on an imaging table that is not level. Distorted images may cause an undesired misdiagnosis of the patient's condition. Second, floating a table that is at an angle is typically more difficult to float. Therefore, leveling an imaging table is typically highly desirable.

Most imaging systems level their respective emitters and detectors to true level. While the emitters and detectors are level to true level, most imaging tables are typically level to the floor on which they are positioned. Therefore, imaging tables are typically mis-aligned with respect to true level.

Currently available systems may employ limit switches to assist in leveling an imaging table. A limit switch is a physical impediment to the angular deviation of the imaging table beyond a pre-defined range. Further, a limit switch is typically fixed to the base of the imaging table. Limit switches, however, may be undesirable because limits switches may yield a large margin of error. Additionally, limit switches are undesirable because limit switches may only level an imaging table with respect to the floor which may not itself be level.

Some imaging tables use tachometer systems to assist in the leveling process of an imaging table. A tachometer system employs tachometers to measure the speed of linear actuators that move the imaging table. The tachometers may determine how fast the actuators, which assist in imaging table positioning, are turning. Alternatively, a tachometer system may determine the angular rotation of a tachometer from a pre-calibrated level position. Tachometer systems, however, may be undesirable because tachometer systems may also yield a large margin of error. Additionally, tachometer systems typically require additional components. Also, tachometer systems may be expensive. Further, tachometer systems, as with limit switches, may only level an imaging table with respect to the floor.

Additionally, typically, limit switches and tachometers are employed to assist leveling an imaging table before the imaging table is floated. However, some imaging tables are re-positioned during imaging. Currently available systems may not be able to level such imaging tables with respect to true level during imaging.

Thus, a need has long existed for an imaging table leveling system that provides more accurate leveling. A need has also existed for an imaging table leveling system that levels an imaging table before and during floating. Also, a need has existed for an imaging table leveling system that levels the imaging table with respect to true level. Additionally, a need has existed for a more cost effective imaging table.

SUMMARY OF THE INVENTION

The present invention includes an imaging table leveling system and method for an imaging table leveling system for use with an imaging table of a medical imaging device. The imaging table leveling system levels an imaging table with respect to true level. The imaging table leveling system levels an imaging table before, or while, the imaging table is floated. The system includes an imaging table, an inclinometer, a processor, and actuators. The inclinometer continuously measures table angle data. When activated, the processor receives the table angle data from the inclinometer. The processor then compares the table angle data to a stored level constant. The processor then commands the actuators to move the imaging table until the table angle data matches the stored level constant. The table angle data is also used to correct differences in actuator rates during tilt, or longitudinal movement, and roll, or lateral movement.

These and other features of the present invention are discussed or apparent in the following detailed description of the preferred embodiments of the invention.

BRIEF DESCRIPTION OF THE DRAWINGS

FIG. 1 illustrates a high level diagram of an imaging table leveling system according to a preferred embodiment of the invention.

FIG. 2 illustrates a structural side view of an imaging table leveling system according to a preferred embodiment of the present invention.

FIG. 3 illustrates a structural front view of an imaging table leveling system according to a preferred embodiment of the present invention.

DETAILED DESCRIPTION OF THE PREFERRED EMBODIMENTS

FIG. 1 illustrates a high level diagram of an imaging table leveling system 100 according to a preferred embodiment of the present invention. The leveling system 100 includes a level key 110, an inclinometer 120, a processing unit 130, and actuators 140. The processing unit 130 includes a stored level constant 135 and a level comparison processor 137.

The level key 110 provides control input to the processing unit 130. The inclinometer 120 measures the table angle data 121 and supplies the table angle data 121 to the processing unit 130. The processing unit 130 compares the table angle data 121 to a stored level constant 135. The processing unit 130 controls the actuators 140.

In operation, the imaging table leveling system 100 may be installed in an imaging table (not shown) in an X-ray imaging device, for example. To level the imaging table, an operator activates the level key 110. The level key 110 then transmits a "level" command to the processing unit 130. The processing unit 130 then directs to actuators 140 to move until the imaging table is level with respect to true level.

The inclinometer 120 measures the angle of the imaging table. The inclinometer 120 supplies the measurement to the processing unit 130 as the table angle data 121. The processing unit 130 receives table angle data 121 from the inclinometer 120. The processing unit 130 then compares the table angle data 121 received from the inclinometer 120 with the stored level constant 135. That is, the processing unit 130 compares the angle of the imaging table with true level. The stored level constant 135 is a previously calibrated constant which is equivalent to true level. Preferably, the stored level constant 135 included within the processing unit 130 has been determined to a margin of error of 0.5° or less laterally or longitudinally from true level. Additionally, the stored level constant 135 is preferably stored in software controlled memory. Because the stored level constant 135 is stored in software controlled memory, the stored level constant 135 may be upgraded.

If the processing unit 130 compares the table angle data 121 and the stored level constant 135 and the table angle data 121 equals the stored level constant 135, then the processing unit 130 does not command the actuators 140 to move because the imaging table is already at true level. If, however, the table angle data 121 and the stored level constant 135 are not equal, then the imaging table is not at true level, and the processing unit 130 directs the actuators 140 to re-adjust the angle of the imaging table to conform to true level. That is, the processing unit 130 directs the actuators 140 to move the imaging table until the table angle data 121 matches the stored level constant 135.

As mentioned above, the imaging table leveling system 100 measures the angular difference between the plane of the imaging table and true level. That is, the imaging table leveling system 100 measures the angle between the imaging table and the level of the earth, rather than the angle between the imaging table and the surface on which the imaging table is positioned.

The imaging table leveling system 100 is preferably calibrated before it is released to the consumer. To calibrate the imaging table leveling system 100, an external leveling device determines a true level constant which is then stored in the processing unit 130 as the stored level constant 135. That is, the external leveling device is placed on the imaging table. Then, the external leveling device determines when the imaging table is level to true level. Then, the processing unit 130 records the determination made by the external leveling device as the stored level constant 135. Because the imaging table leveling system has been calibrated with true level, the imaging table leveling system 100 is then able to measure the angular difference between the present angle of the imaging table as received from the inclinometer 120 and the stored level constant 135 retrieved from the processing unit 130. That is, the imaging table leveling system 100 measures the angular difference between the imaging table's present position and true level.

Preferably the inclinometer 120 is attached to the imaging table in such a way as to be able to determine the angle of the tabletop of the imaging table whereon a patient may be positioned. Preferably, the inclinometer 120 is attached parallel to the imaging table for increased accuracy of angular measurement. The inclinometer 120 continuously measures the present angle of the imaging table and supplies the measurement to the processing unit 130 as the table angle data 121.

In the embodiment described above, the imaging table leveling system 100 levels an imaging table while the imaging table remains stationary. Alternatively, the imaging table leveling system 100 may be employed to continuously level the imaging table while the imaging table is being floated, or positioned. In order to continuously level the imaging table during float, the processing unit 130 continuously compares the table angle data 121 received from the inclinometer 120 to the stored level constant 135 and re-adjusts the angle of the imaging table to conform to true level. That is, the inclinometer 120 continuously transmits table angle data 121 to the processing unit 130. The processing unit 130 compares the table angle data 121 to the stored level constant 135. Because the inclinometer 120 makes real time table angle data 121 measurements, the imaging table leveling system 100 may provide real time corrections during float for tilt and roll movements that threaten the imaging table's alignment with respect to true level, or in the direction that may remain constant. For example, during tilt motion, roll motion may remain constant. The processing unit 130 then directs the actuators 140 to move the imaging table until the table angle data 121 matches the stored level constant 135. If, for example, the actuators 140 are moving at different rates, the processing unit 130 may direct one of the actuators 140 to stop until the other actuator 140 catches up to the other actuator 140. The process of permitting one of the actuators 140 to catch up to the other actuator 140 may minimize tilt motion when the table is rolled or roll motion when the table is titled.

FIGS. 2 and 3 illustrate a structural diagram of the imaging table leveling system 100 of FIG. 1. FIG. 2 illustrates a structural side view of the imaging table leveling system 200 while FIG. 3 illustrates a structural front view of the imaging table leveling system 200. The imaging table leveling system 200 includes a base 210, lift columns 215, a bridge 217, actuator support 218, actuators 142, 144, an inclinometer 120, and a table unit 225. The table unit 225 includes a lower plate 230, lateral bearings 241, lateral bearing rails 242, an upper plate 245, longitudinal bearings 251, longitudinal bearing rails 252, and a tabletop 260. The lower plate 225 is parallel to the upper plate 245 which is parallel to the tabletop 260. The lateral bearings 241 and lateral bearing rails 242 are the lateral system. The lateral system allows lateral float, or roll. The longitudinal bearings 251 and longitudinal bearing rails 252 are the longitudinal system. The longitudinal system allows longitudinal float, or tilt.

The base 210 supports the structure of the imaging table leveling system 200. That is, the base 210 supports the lift columns 215. The lift columns 215 in turn support the bridge 217 which supports the pivot 220. The lift columns 215 also support the actuator support 218 which in turn supports the actuators 142, 144. The pivot 220, along with the actuators 142, 144 support the lower plate 230.

The lower plate 230 supports the lateral system which in turn supports the upper plate 245. The upper plate supports the longitudinal system which in turn supports the tabletop 260. The lateral bearings 241 may be attached on top of the lower plate 230. The lateral bearing rails 241 may be attached to the underside of the upper plate 245. The longitudinal bearings 251 may be attached on the top of the upper plate 245. The longitudinal bearing rails 252 may be attached to the underside of the tabletop 260. Additionally, the inclinometer 120 is attached to the underside of the lower plate 230.

As described above with respect to FIG. 1, in operation, the tabletop 260 is leveled to true level by the imaging table leveling system 100. That is, the level key 110 is activated. The inclinometer 120 continuously transmits table angle data 121. The processing unit 130 receives the table angle data 121 after the level key 110 has been activated. The processing unit 130 then compares the table angle data 121 to the stored level constant 135. The processing unit 130 then commands the actuators 142, 144 to re-adjust the tabletop 260 until the table angle data 121 matches the stored level constant 135.

The actuators 142, 144 move the lower plate 230 in operation with the pivot 220 to level the lower plate 230. That is, as the actuators 142, 144 move the lower plate 230 up or down, the pivot 220 remains in constant contact with the front end of the lower plate 230 and the bridge 217. The lower plate 230 then pivots about the pivot 220 in response to the movement of the actuators 142, 144.

The actuators 142, 144 may tilt the lower plate 230 up or down longitudinally, roll the lower plate 230 from side-to-side laterally, or move the lower plate 230 about a diagonal axis. As the actuators 142, 144 are controlled by the processing unit 130 to extend or recede vertically at the same rate, direction, and at the same time, the lower plate 230 is tilted up or down. That is, if the actuators 142, 144 extend vertically at the same rate, direction, and at the same time, the front end of the lower plate 230 moves upward while the back end of the lower plate 230 moves downward. That is, the front end of the lower plate 230 is tilted up.

As the actuators 142, 144 are controlled by the processing unit 130 to extend or recede vertically at the same rate, and at the same time, but in opposite directions, the lower plate 230 is rolled laterally. That is, if the first actuator 142 extends at the same rate and time as the second actuator 144 recedes, the lower plate 230 moves downward on the second actuator 144 side in a strict lateral, or roll, fashion.

As the actuators 142, 144 are controlled by the processing unit 130 to extend or recede vertically at different rates, the lower plate 230 moves about a diagonal axis. That is, if the first actuator 142 extends or recedes at a different rate as the second actuator 144 extends or recedes, the lower plate 230 moves in a corner-to-corner fashion. For example, if the first actuator 142 is moving at a faster rate than the second actuator 144, corner-to-corner motion may be corrected by stopping the first actuator 142 and allowing the slower second actuator 144 to catch up to the first actuator 142. The processing unit 130 uses table angle data 121 supplied by the inclinometer 120 to determine which actuator 142, 144 to stop and the length of time to keep the motion stopped.

As discussed above, the imaging table may be floated. The tabletop 260 of the imaging table may be floated laterally via the lateral system and longitudinally via the longitudinal system. That is the tabletop 260 may be floated laterally by the lateral bearing rails 242 sliding on the lateral bearings 241. The tabletop 260 may be floated longitudinally by the longitudinal bearing rails 252 sliding on the longitudinal bearings 251. The tabletop 260 may be floated manually by an operator or automatically via an external system (not shown).

Alternatively, the inclinometer 120 may be attached to the upper plate 245 or the tabletop 260 instead of the lower plate 230. Also alternatively, the tabletop may be attached directly to the actuators 142, 144 and the pivot 220 if a floating system is not needed. Also alternatively, an additional actuator may take the place of the pivot, or actuators may be positioned at the four corners of the table. Additionally, the table auto leveling system 200 may be used with a fixed or mobile imaging table.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features which come within the spirit and scope of the invention.

What is claimed is:

1. An imaging table leveling system for use with an imaging table of a medical imaging device, said imaging table leveling system leveling said imaging table with respect to true level, wherein said imaging table includes only a single pivot and wherein said imaging table pivots on said single pivot.

2. The system of claim 1 wherein said imaging table leveling system levels said imaging table before floating said imaging table.

3. The system of claim 2 wherein said imaging table includes a level key automatically leveling said imaging table.

4. The system of claim 1 wherein said imaging table leveling system levels said imaging table while said imaging table is floating.

5. The system of claim 1 wherein said imaging table leveling system includes an inclinometer for measuring the angle of the imaging table and providing said measurement as table angle data.

6. The system of claim 5 wherein said imaging table leveling system includes a processing unit receiving said table angle data from said inclinometer, and said processing unit comparing said table angle data to a stored level constant.

7. The system of claim 1 wherein said imaging table leveling system includes actuators for leveling said imaging table with respect to true level.

8. The system of claim 5 wherein said imaging table leveling system includes:

actuators for leveling said imaging table with respect to true level; and a processing unit for controlling said actuators to continue leveling said imaging table until the table angle data matches a stored level constant.

9. An imaging table leveling system for use with an imaging table of a medical imaging device, said imaging table leveling system including:

an inclinometer measuring the angle of said imaging table and providing said measurement as table angle data;

a processing unit receiving said table angle data forming a comparison of said table angle data to a stored level constant; and a plurality of actuators controlled by said processing unit in response to said comparision, wherein said imaging table leveling system further includes only a single pivot and wherein said imaging table pivots about said single pivot in response to the movement of said actuators.

10. A method for leveling an imaging table of a medical imaging device, said method including the step of leveling said imaging table with respect to true level, wherein said leveling step includes pivoting said imaging table about a single pivot in a medical imaging device having only a single pivot.

11. The method of claim 10 wherein said leveling step includes leveling said imaging table before floating said imaging table.

12. The method of claim 10 wherein said leveling step includes leveling said imaging table while said imaging table is floating.

13. The method of claim 10 wherein said leveling step includes:

measuring the angle of said imaging table with an inclinometer, and providing said measurement as table angle data.

14. The method of 13 wherein said leveling step includes:

receiving said table angle data from said inclinometer with a processing unit, comparing said table angle data to a stored level constant at said processing unit.

15. The method of claim 10 wherein said leveling step includes leveling said imaging table with respect to true level using actuators.

16. The method of claim 13 wherein said leveling step includes:

leveling said imaging table with respect to true level using actators; and controlling said actuators to continue leveling said imaging table until the table angle data matches a stored level constant.

* * * * *